(12) United States Patent
Vesel et al.

(10) Patent No.: US 8,462,911 B2
(45) Date of Patent: Jun. 11, 2013

(54) NUCLEAR MEDICINE SPECT-CT MACHINE WITH INTEGRATED ASYMMETRIC FLAT PANEL CONE-BEAM CT AND SPECT SYSTEM

(75) Inventors: John F. Vesel, Kirtland, OH (US);
Michael J. Petrillo, Pleasanton, CA (US); Ian Farmer, Capitola, CA (US);
Mahmoud Janbakhsh, San Ramon, CA (US); Rizwan Hassan, Danville, CA (US); Paul Hug, Saratoga, CA (US);
Joseph J. Stefan, Milpitas, CA (US);
Marc A. Huber, San Jose, CA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 424 days.

(21) Appl. No.: 12/740,355

(22) PCT Filed: Oct. 29, 2008

(86) PCT No.: PCT/IB2008/054478
§ 371 (c)(1),
(2), (4) Date: Jul. 13, 2010

(87) PCT Pub. No.: WO2009/060344
PCT Pub. Date: May 14, 2009

(65) Prior Publication Data
US 2010/0290584 A1    Nov. 18, 2010

Related U.S. Application Data

(60) Provisional application No. 60/985,789, filed on Nov. 6, 2007, provisional application No. 61/061,237, filed on Jun. 13, 2008.

(51) Int. Cl.
*A61B 6/03* (2006.01)
*H05G 1/00* (2006.01)

(52) U.S. Cl.
USPC .................................. 378/9; 378/210

(58) Field of Classification Search
USPC ................... 378/4, 9, 98.8, 210
See application file for complete search history.

(56) References Cited

U.S. PATENT DOCUMENTS 5,376,795 A   12/1994   Hasegawa et al.
5,391,877 A    2/1995   Marks
(Continued)

FOREIGN PATENT DOCUMENTS

JP   06327662 A   11/1994
JP    9318751 A   12/1997
(Continued)

OTHER PUBLICATIONS

S. Loncaric, W. Chang, and G. Huang, "A Processing Technique for the Truncated Projections of Asymmetric-Fan Beam Transmission Imaging," IEEE Trans. Nucl. Sci., vol. 42, No. 6, pp. 2292-2297, 1995.

(Continued)

*Primary Examiner* — Irakli Kiknadze

(57) ABSTRACT

When performing nuclear (e.g., SPECT or PET) and CT scans on a patient, a volume cone-beam CT scan is performed using a cone-beam CT X-ray source (20) and an offset flat panel X-ray detector (22). A field of view of the X-ray source overlaps a field of view of two nuclear detector heads (18), and the offset of the X-ray detector (22) minimizes interference with nuclear detector head movement about a rotatable gantry (16). Additionally, a locking mechanism (80) provides automatically locking of the X-ray detector (22) in each of a stowed and operation position, improving safety and CT image quality.

30 Claims, 17 Drawing Sheets

U.S. PATENT DOCUMENTS

| | | | |
|---|---|---|---|
| 5,616,117 | A | 4/1997 | Dinkler et al. |
| 6,043,494 | A | 3/2000 | Yamakawa et al. |
| 6,661,865 | B1 | 12/2003 | Popilock |
| 6,670,614 | B1 | 12/2003 | Plut et al. |
| 7,020,233 | B1 | 3/2006 | Tybinkowski et al. |
| 7,075,087 | B2 | 7/2006 | Wang et al. |
| 2003/0001056 | A1 | 1/2003 | Ihalainen et al. |
| 2005/0023471 | A1 | 2/2005 | Wang et al. |

FOREIGN PATENT DOCUMENTS

| | | |
|---|---|---|
| JP | 11009583 A | 1/1999 |
| JP | 2001029336 A | 2/2001 |
| JP | 2003052676 A | 2/2003 |
| WO | 0218714 A1 | 3/2002 |
| WO | 03075763 A2 | 9/2003 |
| WO | 2007018646 A1 | 2/2007 |
| WO | 2008021671 A2 | 2/2008 |

OTHER PUBLICATIONS

P. J. La Riviere, X. Pan, D. Gilland, C. Kao, W. Chang, "Transmission Image Reconstruction and Redundant Information in SPECT With Asymmetric Fanbeam Collimation," IEEE Trans. Nucl. Sci., vol. 48, No. 4, pp. 1357-1363, 2001.

L. Yu, C. Pelizzari, X. Pan, H. Riem, P. Munro, W. Kaissl, "Application of Asymmetric Cone-beam CT in Radiotherapy," IEEE, 0-7803-8700-7/04, pp. 3249-3252, 2004.

J. Gregor, S. S. Gleason, M. J. Paulus, "Conebeam X-Ray Computed Tomography with an Offset Detector Array," IEEE, 0-7803-7750-8/03, pp. II-803-11-806, 2003.

L. A. Feldkamp, L. C. Davis, J. W. Kress, "Practical cone-beam algorithm," J. Opt. Soc. Am., A/vol. 1, No. 6, pp. 612-619, 1984.

G. Wang, "X-ray micro-CT with a displaced detector array," Am. Assoc. Phys. Med. 29 (7), pp. 1634-1636, 2002.

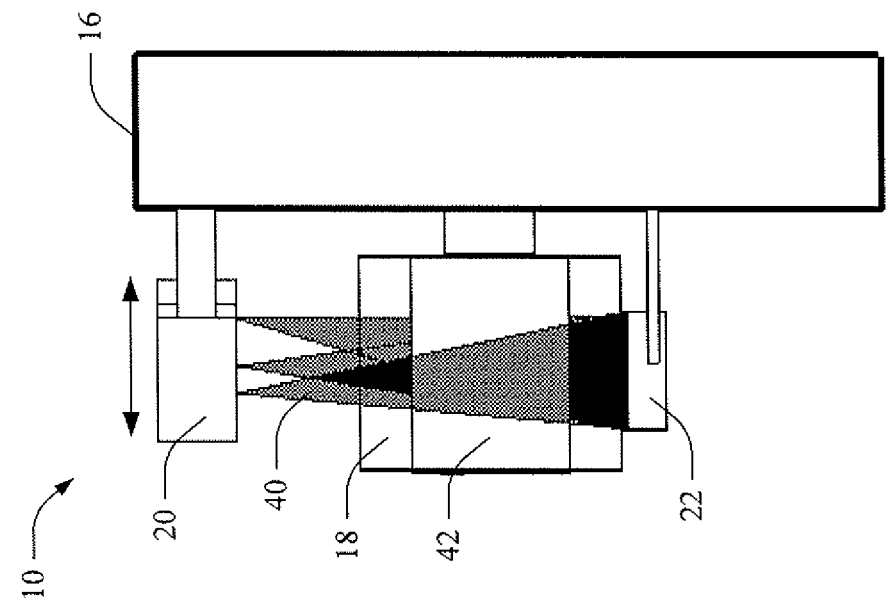
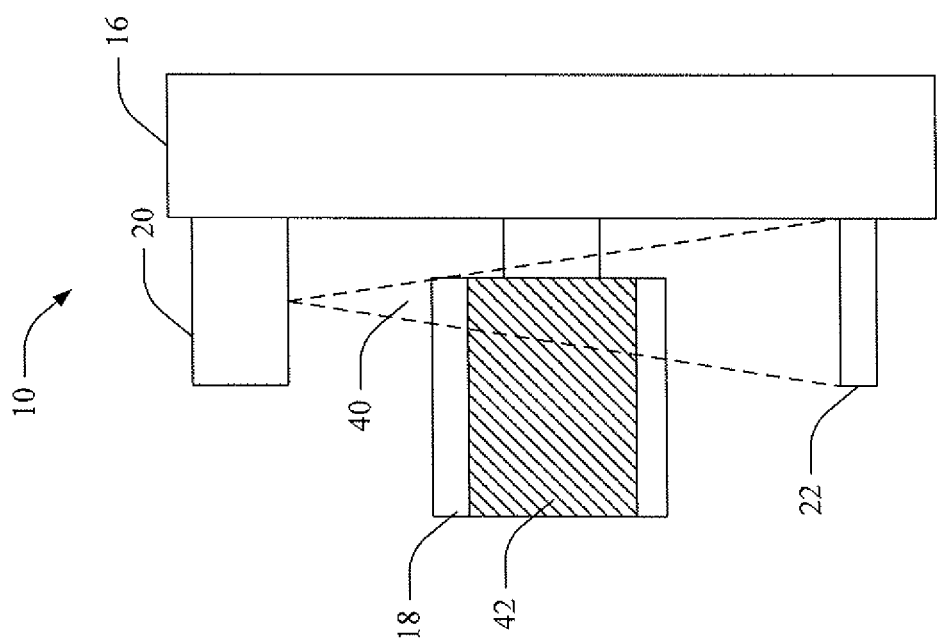
FIG. 2D
FIG. 2C

NUCLEAR MEDICINE SPECT-CT MACHINE WITH INTEGRATED ASYMMETRIC FLAT PANEL CONE-BEAM CT AND SPECT SYSTEM

CROSS REFERENCE TO RELATED APPLICATIONS

This application claims the benefit of U.S. provisional application Ser. No. 60/985,789 filed Nov. 6, 2007 and U.S. provisional application Ser. No. 61/061,237 filed Jun. 13, 2008, both of which are incorporated herein by reference.

The present application finds particular application in diagnostic imaging systems, particularly involving cone-beam computed tomography (CT) and single photon emission computed tomography (SPECT). However, it will be appreciated that the described technique may also find application in other imaging systems, other medical scenarios, or other medical techniques.

Typical commercial system designs, such as Philips Precedence, Philips Gemini, Siemens Symbia, etc., that combine both nuclear medicine (NM) and X-ray CT modalities are configured in an in-line geometry. In this configuration, a common patient table extends between two imaging field-of-view (FOV) regions that are separated in the axial direction by the space between the NM and CT gantries.

In other commercial system designs, such as the GE Hawkeye, an x-ray source and CT detector are mounted a common gantry with the NM detectors, but are still separated in the axial direction. Others have proposed concepts using flat panel detectors mounted on a common gantry. When the CT and NM detectors are axially displaced, there is axial movement and temporal offset between NM and CT data acquisitions. This raises issues concerning subject motion between the NM and CT data acquisitions and alignment.

Reconstruction for asymmetric detector configurations have been published for extending the FOV for SPECT detector systems using radiation sources. Radiation therapy systems have integrated imaging to more precisely target tumors using flat panels that have been configured to support a larger imaging FOV. Additionally, pre-clinical systems have used an asymmetric detector geometry that makes use of volume CT reconstruction.

When combining two different technologies together, such as a SPECT Gantry with an X-Ray Gantry (C-Arm) several challenges arise. Integrating these two systems into one gantry involves additional packaging constraints and SPECT detector motions that can cause interference with X-Ray components. For instance, once deployed, a flat panel X-ray detector needs to be accurately positioned and held stable to reduce artifacts. Additionally, it is desirable that deployment is repeatable at the same position.

The present application provides new and improved hybrid nuclear medicine/CT systems and methods that improving image acquisition and reconstruction time, which have the advantages of improving patient scan speed and quality, and which overcome the above-referenced problems and others.

In accordance with one aspect, a hybrid patient imaging system, includes at least two nuclear detector heads mounted on a rotatable gantry, an X-ray source mounted on the gantry, and an X-ray detector mounted on the gantry opposite the X-ray source and offset relative to the X-ray source, wherein a field of view (FOV) of the X-ray source and a FOV of the nuclear detector heads overlap each other.

In accordance with another aspect, a hybrid subject imaging system, includes an automatic-locking extender arm, hingeably coupled by a hinge pin to a mount on a rotatable gantry and including an extendible slider plate that is coupled to a flat-panel X-ray detector, a cone-beam X-ray source coupled to the gantry opposite the X-ray detector, the X-ray source being movable in a longitudinal direction along a volume of interest (VOI), parallel to a longitudinal axis through the gantry, and two nuclear detectors coupled to the gantry and having a FOV that overlaps with a FOV of the X-ray source. The extender arm rotates about the hinge pin approximately 90° between a stowed position flush against the mount and an operational position in which an X-ray receiving surface of the X-ray detector is slightly offset from, and faces, the X-ray source.

In accordance with yet another aspect, a method of locking a flat panel X-ray detector in each of a stowed position and an operational position, includes extending a slider plate outward to a first position from an extender arm that is coupled to a mount on a gantry, wherein a first motion translator translates linear motion from a slider coupled to the slider plate into rotational motion that is applied to a locking pin screw to back a locking pin out of a first receiving bore and unlock the detector from a stowed position. The method further includes rotating the extender arm approximately 90° from the stowed position to the operational position, and extending the slider plate to a second position wherein a second motion translator translates linear motion from a slider coupled to the slider plate into rotational motion that is applied to a locking pin screw to translate the locking pin into a second receiving bore and lock the detector in an operational position. The slider plate is coupled to the X-ray detector, which is oriented toward an X-ray source when in the operational position.

In accordance with another aspect, a method of hybrid imaging comprises rotating at least two nuclear detector heads, an X-ray source, and an X-ray detector around a patient pallet such that a field of view of the X-ray source and detector is coincident with a field of view of the nuclear detector heads, and, during CT imaging, collecting truncated portions of a VOI of a patient in such a manner that views from opposite halves of the VOI are collected in 180° opposite rotational orientations of a rotating gantry.

In accordance with another aspect, a hybrid subject imaging system includes a locking extender arm, rotatably coupled by a first pivot point to a flat-panel X-ray detector and rotatably coupled by a second pivot point to a rotatable gantry, and a cone-beam X-ray source coupled to the gantry opposite the X-ray detector, the X-ray source being movable in a longitudinal direction along a volume of interest (VOI), parallel to a longitudinal axis through the gantry. The system further includes two nuclear detectors coupled to the gantry and having a field of view (FOV) that overlaps with a FOV of the X-ray source. The extender arm rotates about the second pivot point approximately 90° between a stowed position flush against the gantry, and the flat-panel X-ray detector rotates about the second pivot point approximately 180°, to an operational position in which an X-ray receiving surface of the X-ray detector is slightly offset from, and faces, the X-ray source.

One advantage is that data acquisition time is reduced, as is the interval between NM and CT data acquisitions.

Another advantage resides in inherently aligned NM and CT data and images.

Another advantage resides in automated locking of a flat panel X-ray detector.

Still further advantages of the subject innovation will be appreciated by those of ordinary skill in the art upon reading and understanding the following detailed description.

The innovation may take form in various components and arrangements of components, and in various steps and arrangements of steps. The drawings are only for purposes of illustrating various aspects and are not to be construed as limiting the invention.

FIG. 1 illustrates an imaging system includes a subject support, such as a table or couch, which is selectively positionable up and down to position a subject being imaged or examined at a desired location, for instance, so that regions of interest are centered about a longitudinal axis.

FIG. 2A diagrammatically illustrates a front view of the integrated hybrid system, which includes two nuclear detectors, X-ray or CT source, and flat panel X-ray or CT detector that is mounted asymmetrically to a common rotation center of the gantry.

FIG. 2B diagrammatically illustrates a side view of the integrated hybrid system of FIG. 2A, wherein the imaging FOVs between the two systems is common or coincident, requiring little or no movement of the patient, providing commonly registered images due to the similar imaging planes.

FIG. 2C diagrammatically illustrates another side-view of the system of FIG. 2B, wherein the CT source and detector have been moved to a retracted position along the longitudinal axis.

FIG. 2D diagrammatically illustrates a side view of the gantry wherein the CT source moves longitudinally parallel to a central longitudinally axis through the gantry, while emitting an X-ray cone beam through the VOI.

FIG. 2E diagrammatically illustrates a side view of another embodiment of the system, wherein the CT X-ray source and flat panel detector are in an in-line configuration relative to the nuclear detector heads. In this embodiment, a volume of interest (VOI) can be imaged using the nuclear detector heads and the CT source and detector sequentially (in either order).

The systems and methods described herein relate to combining a cone-beam CT (CBCT) source with an offset flat panel detector and nuclear imaging heads in a single patient imaging device. By using an offset flat panel detector, the size of the detector can be minimized, as compared to a full-sized CT detector, thereby occupying less space and permitting greater freedom of movement of the nuclear imaging heads. Nuclear imaging provides physiological process and/or functional information that can be used for diagnosis, to assess the effectiveness of therapy, etc. The addition of another modality, such as CBCT that is co-registered is useful in improving the clinical confidence of the reader. Additionally, the CBCT information can be used to correct for attenuation of emission data, improving the quantitative accuracy and the quality of the images.

Other features relate to a locking mechanism that ensures that the flat panel detector stays in place during CBCT scans and stows out of the way when the CBCT source is not in use, such as during a nuclear imaging (NM) scan or during system downtime.

Figure 1:
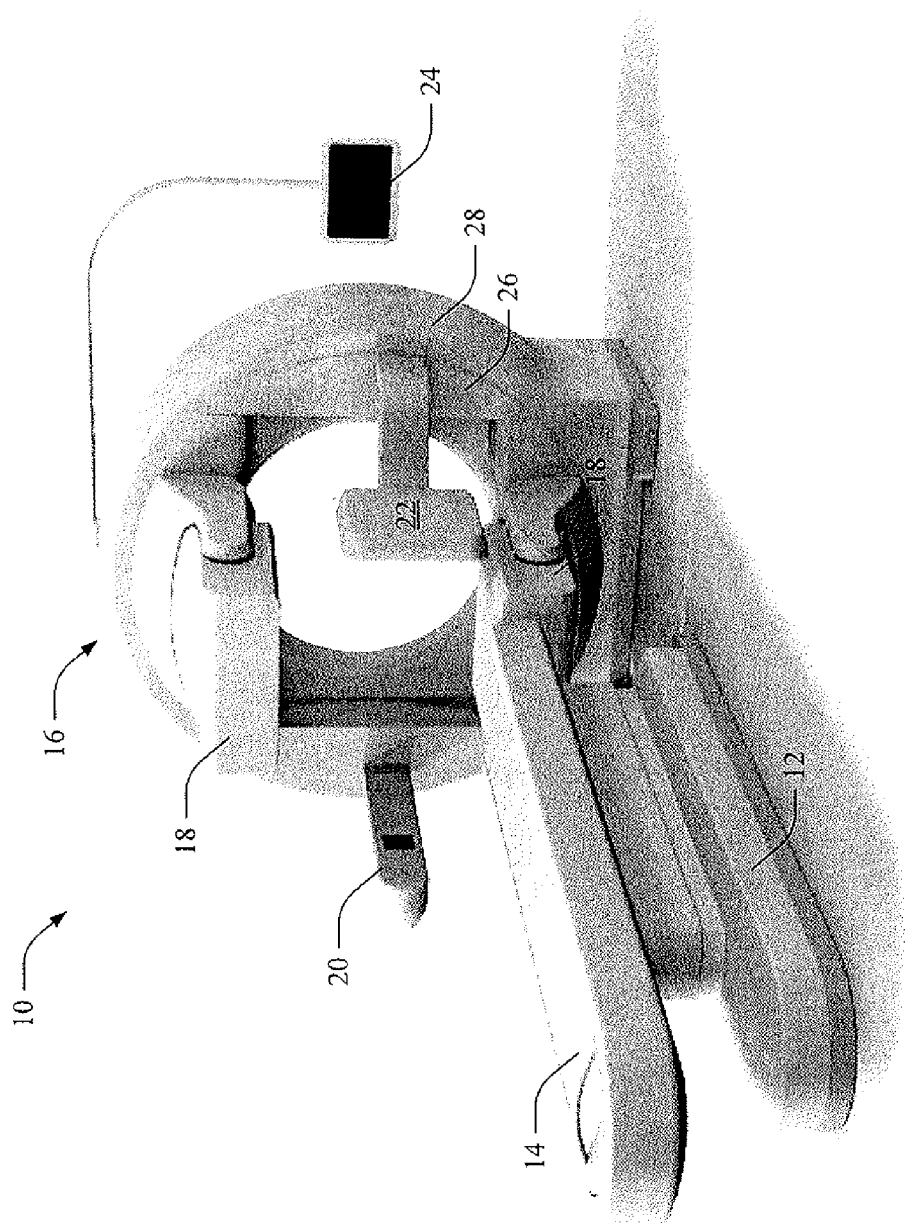

With reference to FIG. 1, an imaging system 10 includes a subject support 12, such as a table or couch, which is selectively positionable up and down to position a subject being imaged or examined at a desired height, for instance, so that a volume of interest of the patient is centered about a longitudinal axis of the imaging system. The table includes a pallet 14 that is moveable parallel to the longitudinal axis through a rotatable gantry 16, such that the volume of interest (VOI) of the patient can be translated into the field of view (FOV) of the imaging system for imaging by nuclear detector heads 18 (e.g., gamma cameras or the like) and/or by a CBCT X-ray source 20 and a flat panel CBCT or X-ray detector 22. A motive power source (not shown), such as a motor, selectively drives the pallet parallel to the longitudinal axis to position the VOI in the FOV. Detected patient image data (e.g., nuclear and/or CT data) is received by a workstation (not shown), which includes appropriate hardware and software for performing image reconstruction and the like to generate images for viewing by an operator on a monitor 24.

An inner gantry structure 26 is rotatably mounted on the outer gantry structure 28 for stepped or continuous rotation. The nuclear detector heads 18 rotate as a group about the subject, when received, with the rotation of the rotating gantry structure 26. The detector heads are radially, circumferentially, and laterally adjustable to vary their distance from the subject and spacing on the rotating gantry 26 to position the detector heads in any of a variety of angular orientations about, and displacements from, the central axis. For example, separate translation devices, such as motors and drive assemblies, are provided to independently translate the detector heads radially, circumferentially, and laterally in directions tangential to the subject (e.g., along linear tracks or other appropriate guides). The embodiments described herein employing two detector heads can be implemented on a two detector system, a three detector system, or the like. Likewise, the use of three-fold symmetry to adapt the illustrated embodiments to a three detector system is also contemplated.

In one embodiment, the nuclear detector heads are SPECT detector heads. In SPECT imaging, a projection image representation is defined by the radiation data received at each coordinate on the detector head. In SPECT imaging, a collimator defines the rays along which radiation is received.

In another embodiment, the nuclear detector heads are positron emission tomography (PET) detector heads. In PET imaging, the detector head outputs are monitored for coincident radiation events on two heads. From the position and orientation of the heads and the location on the faces at which the coincident radiation is received, a ray or line of response (LOR) between the coincident event detection points is calculated. This LOR defines a line along which the radiation event occurred. In both PET and SPECT, the radiation data from a multiplicity of angular orientations of the heads is then reconstructed into a volumetric image representation of the volume of interest.

The CBCT source 20 can be segmented into a plurality of regions such that only a portion of the field of view (FOV) is imaged at a time during a scan, for instance, by employing a collimator and/or an axial filter suitable for CT imaging, as discussed below with regard to FIG. 3.

The CBCT source 20 rotates around the FOV such that both CT and emission imaging FOVs are coincident or overlapping with limited or no movement of the pallet 14. The flat panel radiation detector 22 is placed in an asymmetric geometry relative to the rotation center so that the CT FOV is sufficient to image patients without truncation. Additionally, the flat panel detector facilitates generating high-resolution radiographic data that can be interpreted as radiograms. Thus, system 10 is a multi-modality system that eliminates or reduces registration problems between nuclear imaging (e.g., SPECT, PET, etc.) and CT or other modality images, since the displacement between the two imaging planes is significantly reduced or eliminated compared to in-line systems. This also reduces the requirements on the room size for a combined scanner, since the patient support does not need to be extended to different FOVs of two separate imaging systems. Complexity and cost of the site preparation is thereby reduced, and retroactive installation of SPECT/CT or PET/CT systems in existing facilities is facilitated.

By using an asymmetric detector geometry, the flat panel detector 22 can be reduced in size to accommodate conventional motions of the nuclear detectors 18, mitigating clearance issues that may arise if a larger CT detector were used. Furthermore, no additional cost is associated with the patient table since no modification is required thereto over existing SPECT or PET imaging table configurations (e.g., because the nuclear imaging FOV and the CT imaging FOV are coincident). Furthermore, the FOV of the CT can be increased (e.g., doubled to approximately 50 cm or more), allowing the scanning of large patients without truncation. Additionally, nuclear detector head rotation speed can be limited by weight and safety constraints. Conversely, a volume CBCT acquisition and reconstruction enables large axial coverage in one rotation. This reduces the overall scan time and permits breath-hold acquisitions, thereby improving image quality.

Figure 2B:
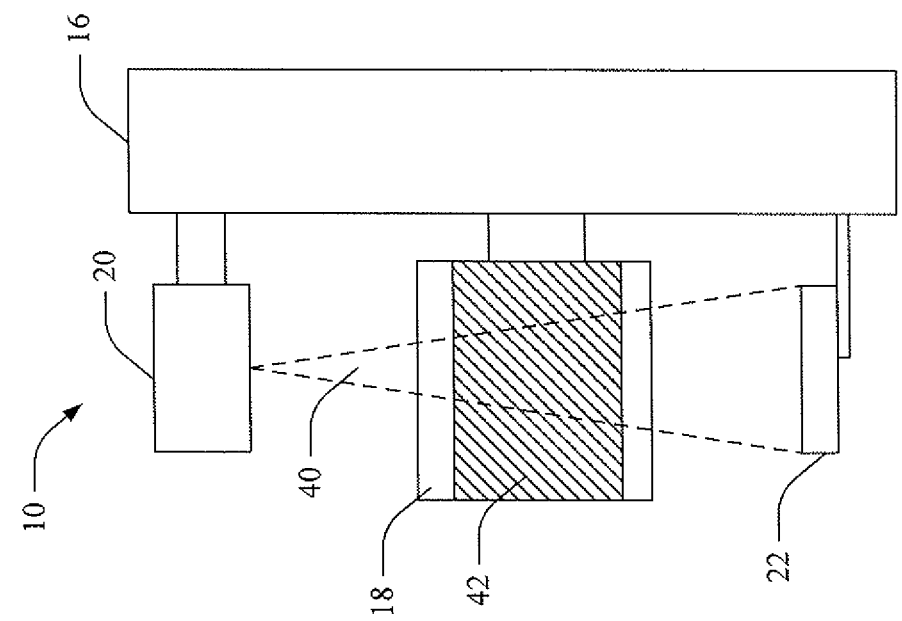
Figure 2A:
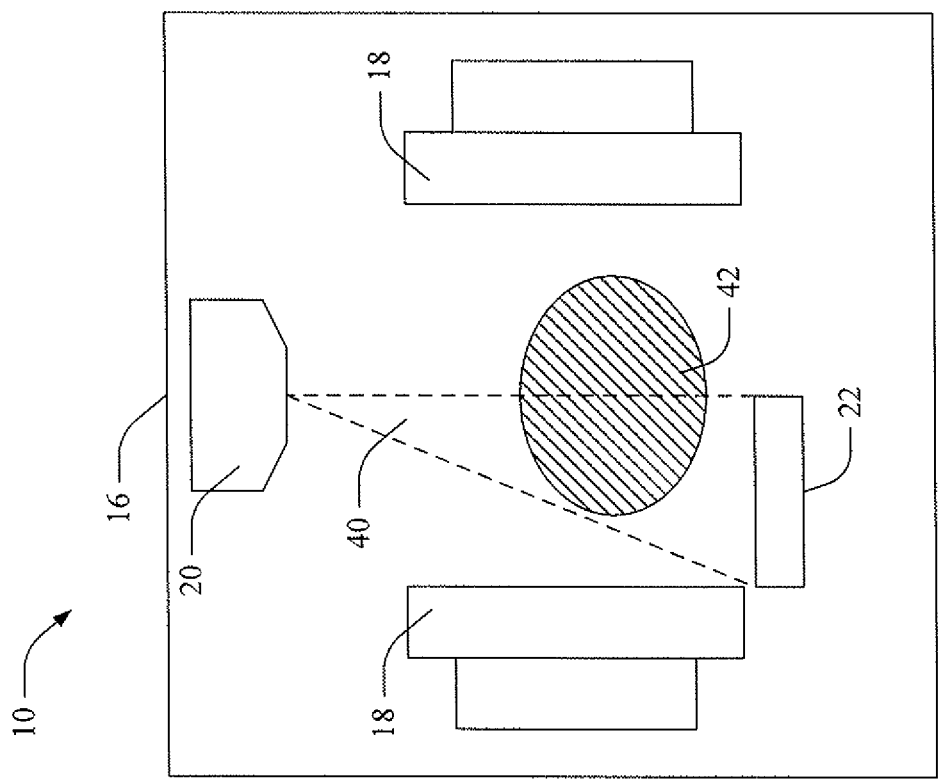

FIG. 2A illustrates the integrated hybrid system 10, which includes two nuclear detectors 18, X-ray or CT source 20, and flat panel X-ray or CT detector 22 that is mounted asymmetrically to a common rotation center of the gantry 16. The nuclear detectors are shown in a 180° configuration, such as for a whole-body planar, SPECT, or PET scanning protocol. The CT source 20 emits an asymmetrical beam, such as may be generated using a beam filter, collimator, (not shown) or the like, directed onto the asymmetrically aligned CT detector 22. The CT detector can be moved to a plurality of positions to generate overlapping FOVs 40 of the VOI 42 in order to generate a complete CT image of the VOI. Note that when the gantry has rotated 180°, the radiation beam will image the other half of the VOI.

FIG. 2B illustrates a side view of the system 10, wherein the imaging FOVs between the two systems is common or coincident, requiring little or no movement of the patient, providing commonly registered images due to the similar imaging planes. The gantry can be rotated 360° degrees during the CT acquisition so that an entire projection dataset that encompasses the patient is acquired once the truncated opposing views (180°) are weighted together. The detector 22 can be offset to create overlap between the opposing projections without missing data. Offsetting or misaligning the detector reduces image artifacts by reducing truncated projection data. Reconstruction using algorithms such as the Feldkamp algorithm can then be used to generate volume CT datasets that can be used for either anatomical localization or attenuation correction. Motion of the X-ray source during the rotation can achieve complete sampling, improving the CBCT reconstruction.

FIG. 2C illustrates another side-view of the system 10, wherein the CBCT source 20 is offset toward the gantry 16 to show motion of the CT source along the longitudinal axis through the gantry, in addition to rotation about the circumference of the gantry. The CT source can thus be extended and/or retracted to scan the length of the VOI, in addition to being rotated about the VOI, to generate a complete set of image data from plurality of angles and positions. During rotational movement of the gantry, the nuclear detectors 18 are held stationary relative to the CT source and detector, so that all devices move with the gantry to ensure that the nuclear detectors are kept out of the FOV of the CT heads and vice versa.

FIG. 2D illustrates a side view of the gantry 16 wherein the CT source 20 moves longitudinally parallel to a central longitudinal axis through the gantry, while emitting an X-ray cone beam through the VOI 42. The longitudinal motion of the CT source facilitates scanning the entire VOI, without having to move the VOI, and can be performed while the gantry is rotated (e.g., continuously or in a stepping action) to ensure that no portion of the VOI is missed during the CT scan. Additionally, the detector 22 can be moved longitudinally with the CT source, or can remain stationary. A filter (not shown) can be employed to direct the X-ray beam toward the detector 22, whether the detector is moving or stationary. In this manner, the system 10 mitigates problems that can arise due to incomplete sampling.

Figure 2E:
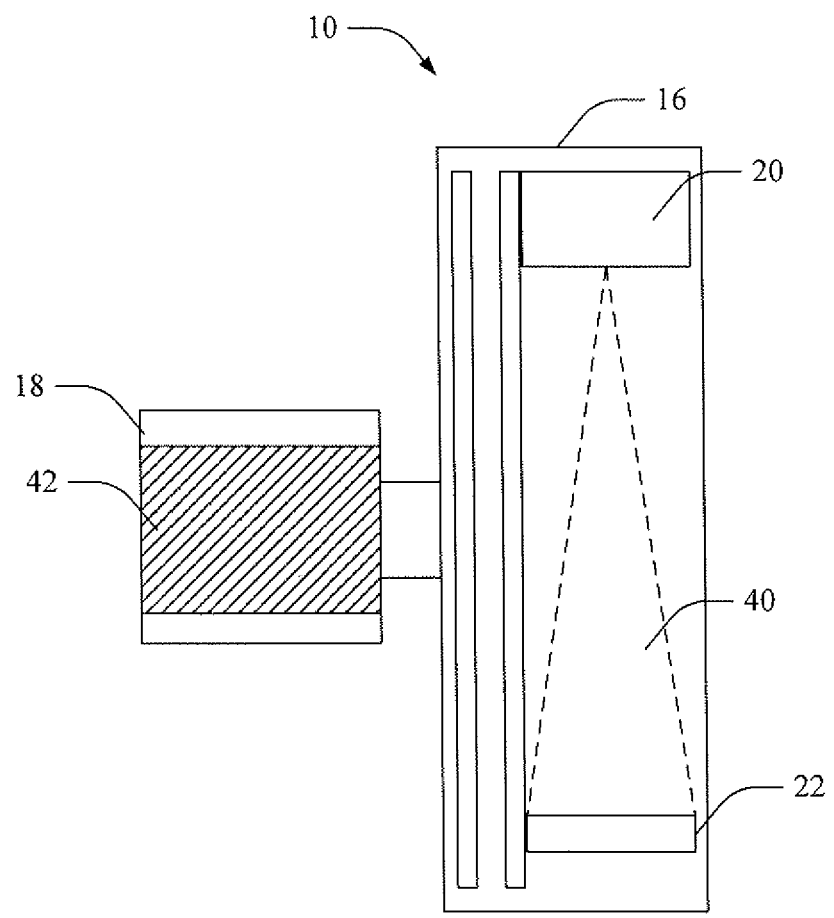

FIG. 2E illustrates another side view of the system 10, wherein the CT X-ray source 20 and flat panel detector 22 are in an in-line configuration relative to the nuclear detector heads 18. In this embodiment, a VOI can be imaged using the nuclear detector heads and the CT source and detector sequentially (in either order).

Figure 3:
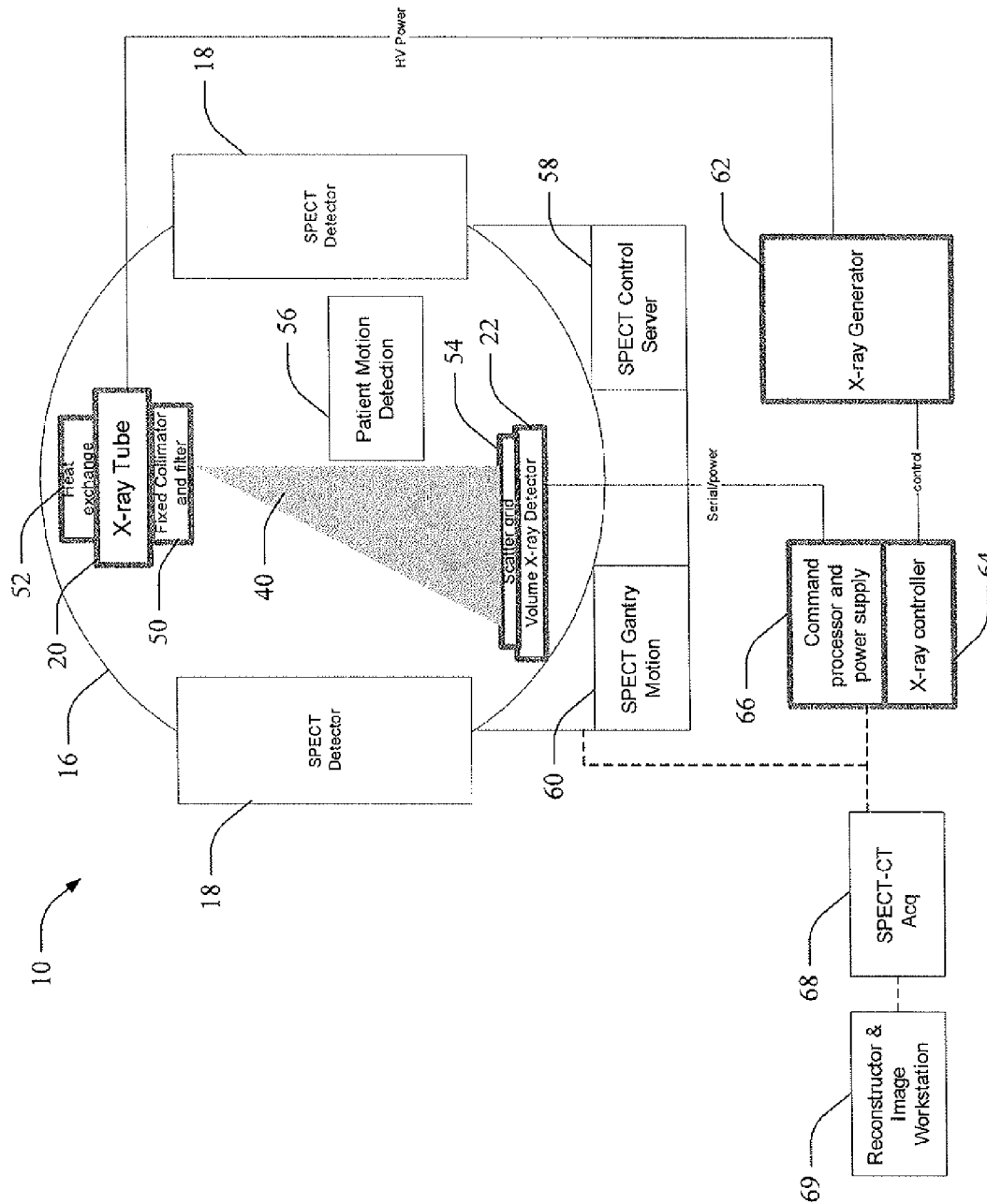
FIG. 3 is an illustration of another embodiment of the imaging system with a collimator and filter device for directing all or a portion of a cone-shaped X-ray beam to an offset flat panel detector.

FIG. 3 is an illustration of another embodiment of the imaging system 10 with a collimator and filter device 50 for directing all or a portion of a cone-shaped X-ray beam to an offset flat panel detector. The system includes the gantry 16, which receives a pallet (not shown) that is supported by a table support (not shown) as it is inserted into an imaging region of the gantry. A pair of nuclear detectors 18 (e.g., SPECT detectors, PET detectors, etc.) are movably positioned on the gantry, along with the X-ray source 20 and the flat panel detector 22. The X-ray source includes a heat exchange device 52 for dissipating heat when the X-ray source is in use. Additionally, a scatter grid 54 is positioned between a VOI (not shown) and the flat panel detector 22. The scatter grid absorbs scattered or attenuated X-rays while letting primary X-rays through to the detector in order to improve X-ray detection.

A patient motion detector 56 detects patient motion, which can trigger adjustment of the CT and/or nuclear imaging detectors to ensure that the VOI of the patient remains within the FOVs thereof. For instance, detected patient motion can trigger a control server 58 and/or a gantry motion controller 60 to initiate movement of the detectors 18 and/or CT source and detector system and/or the patient pallet, respectively, supplies power to maintain the patient in the FOV 40.

An X-ray generator 62 supplies power to the X-ray source 20 to generates X-rays to be emitted through the source during a CT scan. The X-ray generator is additionally coupled to an X-ray controller 64 that signals the X-ray generator to generate X-rays at appropriate times, with appropriate intensity, etc., during the CT scan. The controller 64 is also coupled to a command processor 66 (with a power supply) that receives detected X-ray information from the flat panel detector 22 and provides power thereto. The command processor is additionally coupled to the gantry and to a SPECT-CT acquisition component 68 that receives detected SPECT and CT data. A workstation 69 receives acquired data and includes reconstruction processors and memory (not shown) for reconstructing CT and nuclear images of the VOI or patient.

Figure 4:
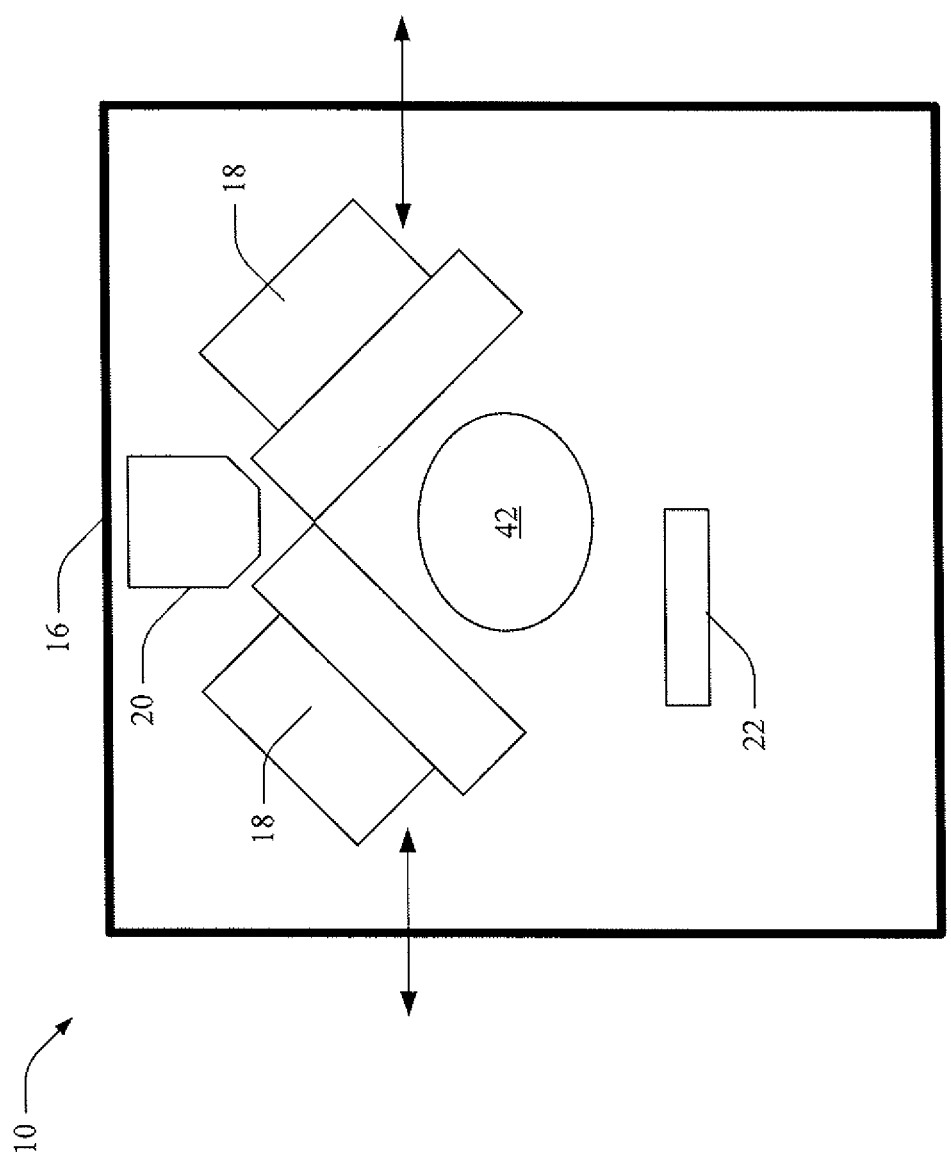
FIG. 4 illustrates the system configured in a geometry with the NM detector at a 90° angle that is typically used during a nuclear cardiology exam.

FIG. 4 illustrates the system 10 configured in a geometry that is typically used during a nuclear cardiology exam. The CT source 20 is positioned on the gantry in a manner that does not impede motion of the nuclear detectors 18 into a 90° orientation, relative to each other, which is desirable when performing a cardiology scan. The nuclear detectors are laterally (in the depicted orientation) moveable to permit the CT source to emit an X-ray beam for detection by the flat panel detector 22 when desired.

Figure 5:
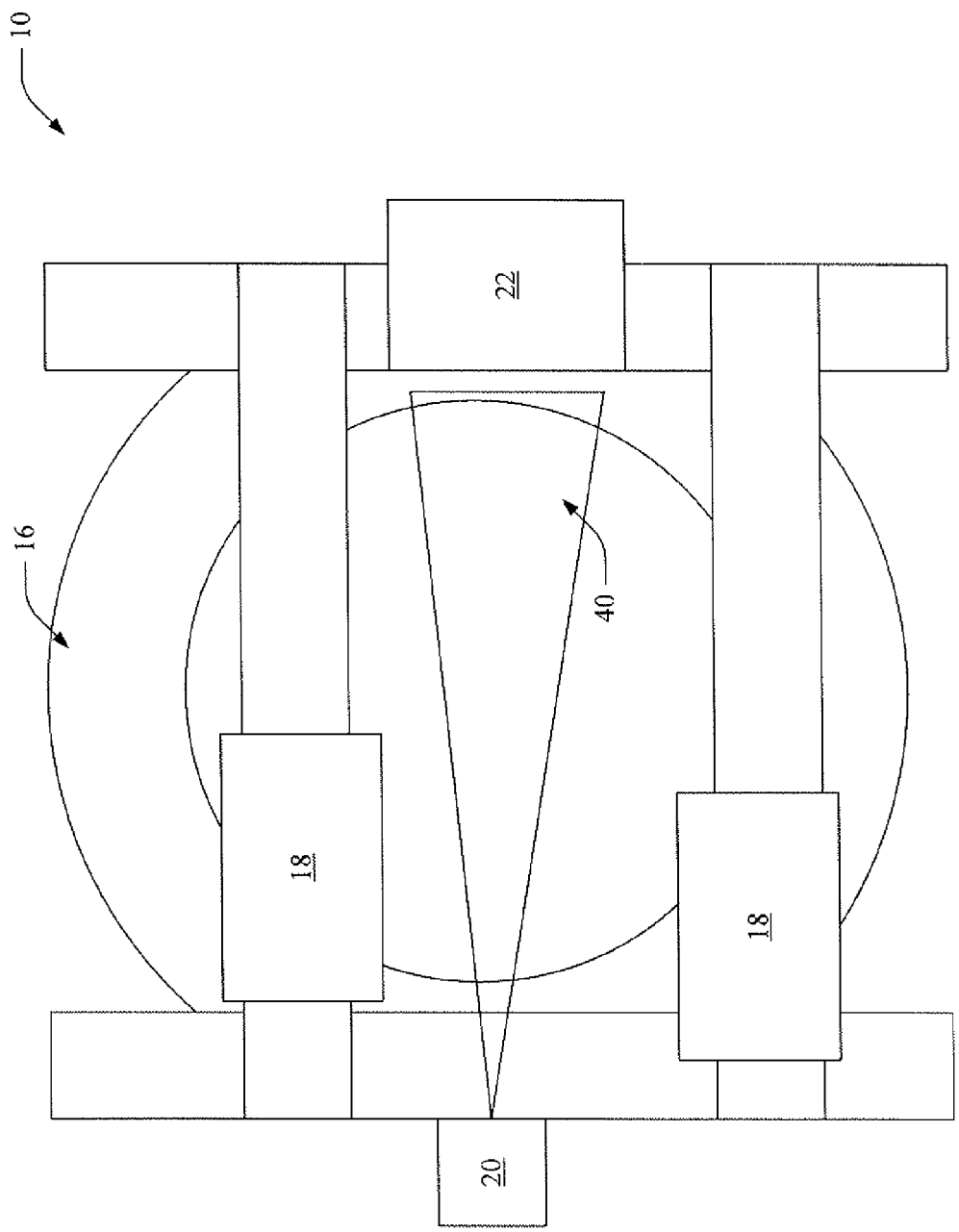
FIG. 5 illustrates another embodiment of the system, wherein the nuclear detectors (e.g., SPECT or PET), the CT source, and the flat panel detector are movably mounted on tracks that facilitate positioning the devices at desired locations during CT and/or nuclear scans and moving components that are not currently in use out of the way of those that are.

FIG. 5 illustrates another embodiment of the system 10, wherein the nuclear detectors 18 (e.g., SPECT or PET), the CT source 20, and the flat panel detector 22 are movably mounted on tracks that facilitate positioning the devices at desired locations during CT and/or nuclear scans. The nuclear detector heads are mounted to a frame that moves along a circular path. The nuclear detectors translate along the sections of the frame, which move closer and further from each other to move the detector heads in a controlled, complex path about the gantry 16. The X-ray source and detector move on circular path around the gantry and are attached thereto by retractable arms that move along frame sections perpendicular to the nuclear detectors and the central axis through the gantry (e.g., up and down in the rotational orientation of FIG. 5). The motion of a retractable extender arm, as it unfolds, is employed to automatically lock for the arm to lock the X-ray detector in a desired position (shown in a stowed or folded position in FIG. 5). In one embodiment, the flat panel detector is attached to a linear slider arm that allows the detector to fold and unfold. The arm is attached to a beam that moves in a circular path and includes an automatic mechanical lock. In this manner, the system 10 mitigates a need for manual locking of the detector 22.

Figure 6:
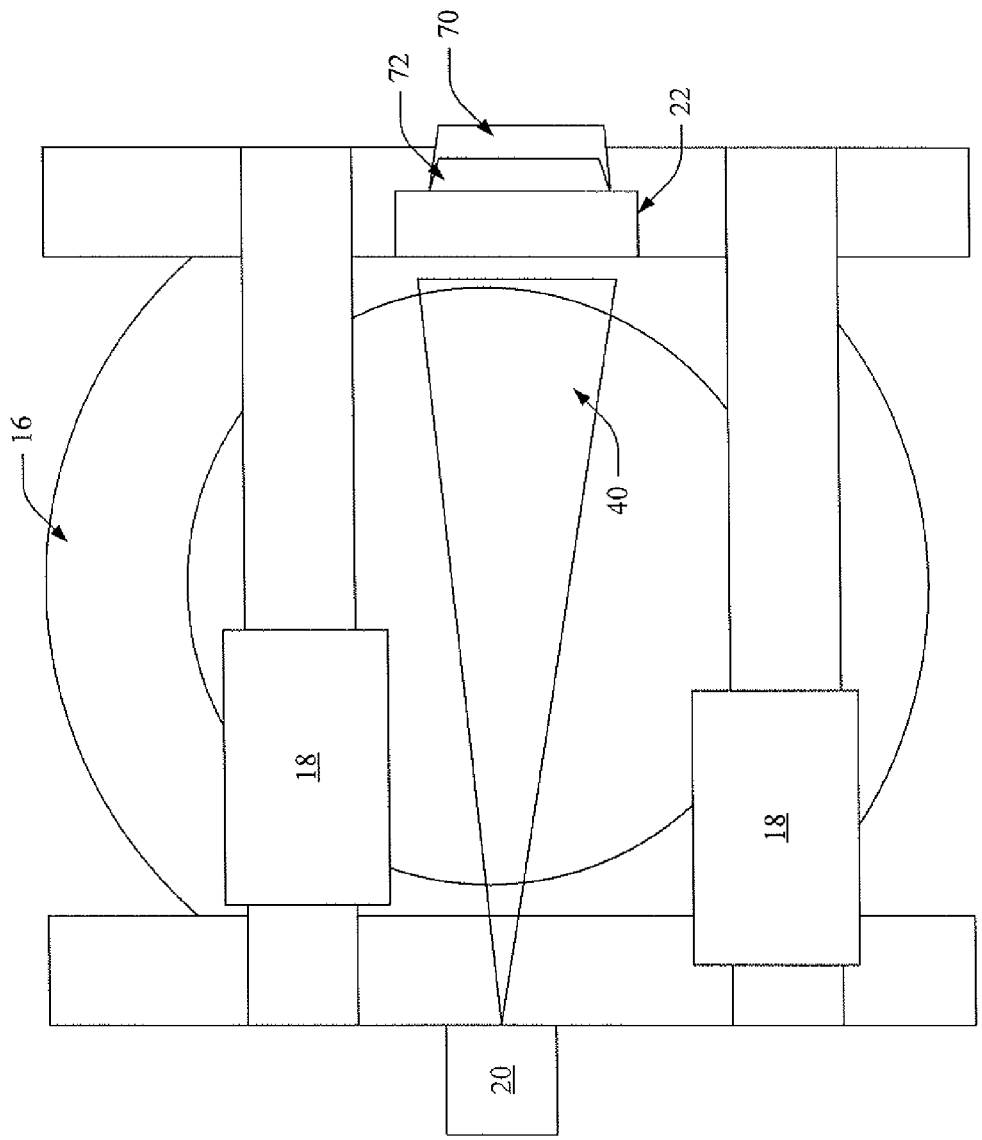
FIG. 6 is a perspective view of the system, wherein the flat panel detector is in its operational position, extended outward on an extender that is lockably coupled to a mount that couples the extender and flat panel detector to the gantry.

FIG. 6 is a perspective view of the system 10, wherein the flat panel detector 22 is in its operational position, extended outward on an extender arm 70 that is lockably coupled to a mount 72 that couples the extender arm and flat panel detector to the gantry 16. The CT source 20 emits an X-ray beam across an FOV to the flat panel detector while nuclear detectors 18 are positioned out of the way (e.g., off to the side). In the illustrated view, the extender arm extends outward from the page.

Figure 7:
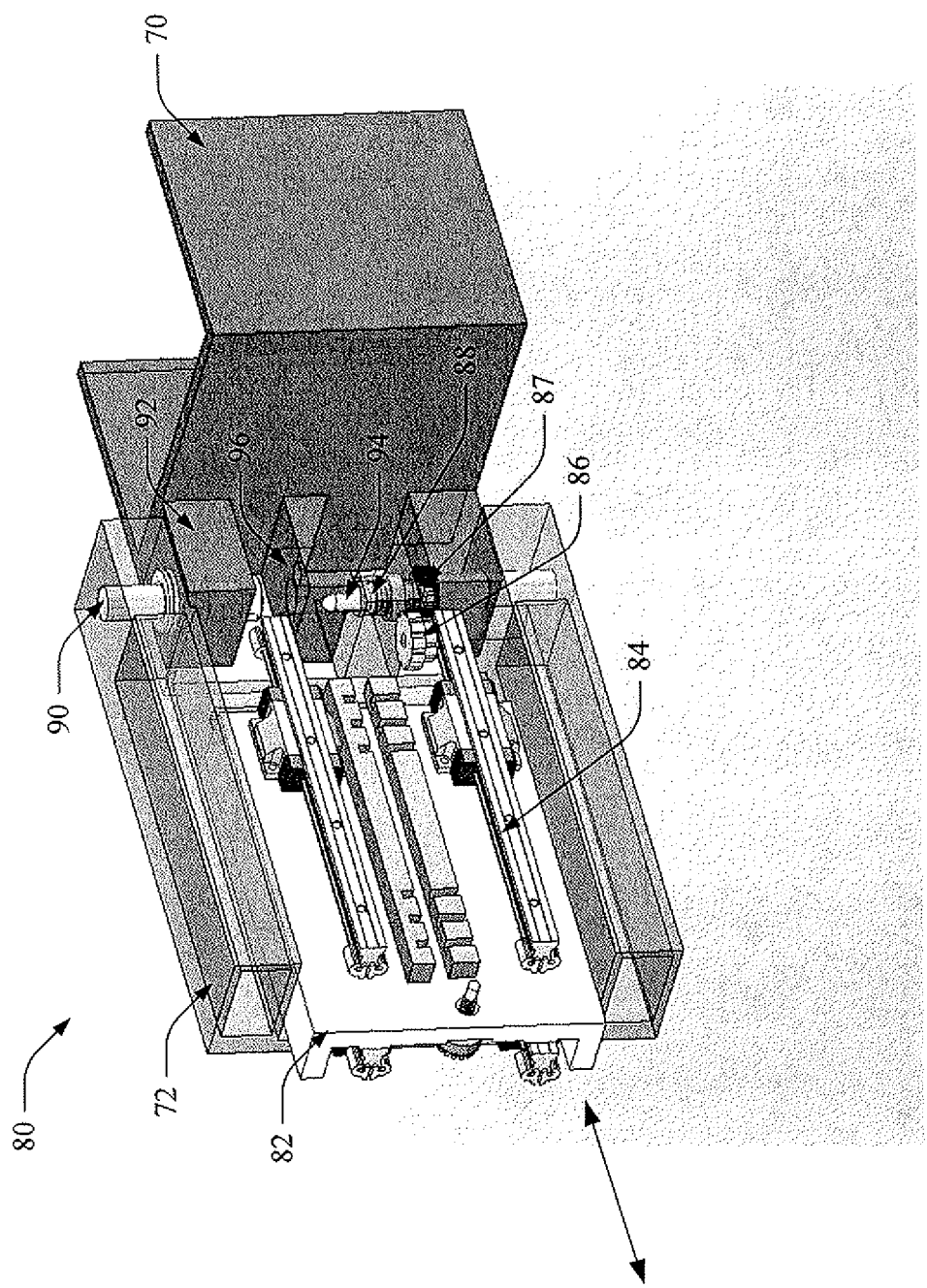
FIG. 7 is a perspective view of an automatic locking mechanism for locking the flat panel detector in one or more positions, shown with the extender arm in its extended position.

FIG. 7 is a perspective view of an automatic locking mechanism 80 for locking the flat panel detector in one or more positions, shown with the extender arm 72 in its extended position. The mechanism includes the mount 70 with the extender arm 72 coupled thereto in a hinged arrangement. The extender includes a slider plate 82 with a plurality of extendible sliders 84 along which the slider plate moves when being extended. At least one slider 84 is coupled to a motion translator 86 that translates the linear motion of the slider into rotational motion. In one embodiment, the motion translator is a gear that is turned by a rack and pinion system (not shown) inside the slider, such that when the slider is extended, the gear rotates in a first direction, and when the slider is retracted the gear rotates in an opposite direction.

The hinged coupling between the mount 70 and the extender arm 72 includes a pin 90 that extends through the ends of an upper and lower portion of the extender arm and through a plurality of hinge segments 92. The gear is in mechanical contact with a locking pin screw 88, and when the gear rotates in the first direction, it causes the locking pin screw to turn and extend a locking pin 94. The locking pin is received by a bore 96 and locks the extender arm 72 in position when the detector is fully extended.

Figure 8:
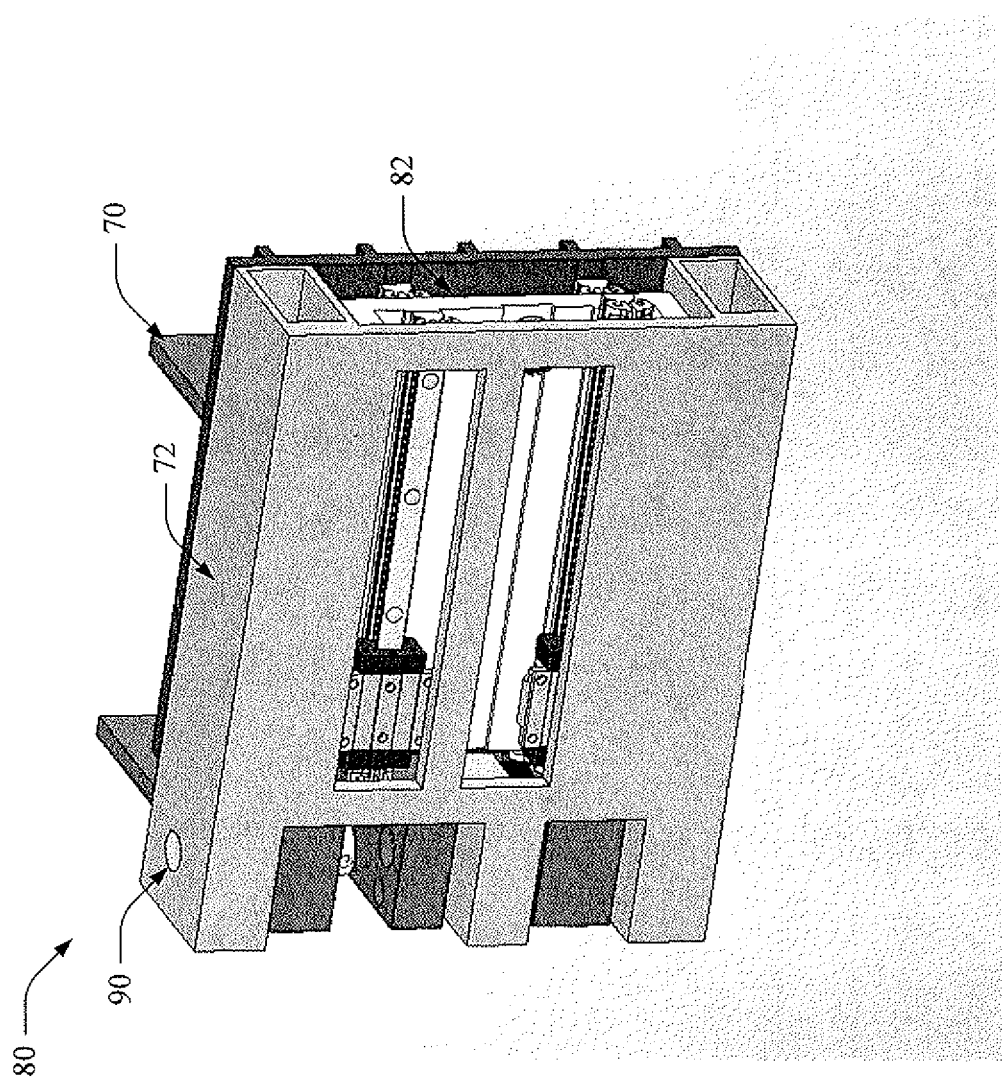
FIG. 8 illustrates the automatic locking mechanism for the flat panel CT detector in its stowed position.

FIG. 8 illustrates the automatic locking mechanism 80 for the flat panel CT detector in its stowed position. The extender arm 72 is stowed against the mount 70 (e.g., the extender arm 72 has been pivoted about the hinge pin 90 to a stowed position). The slider plate 82 is fully retracted into the extender arm 72.

Figure 9:
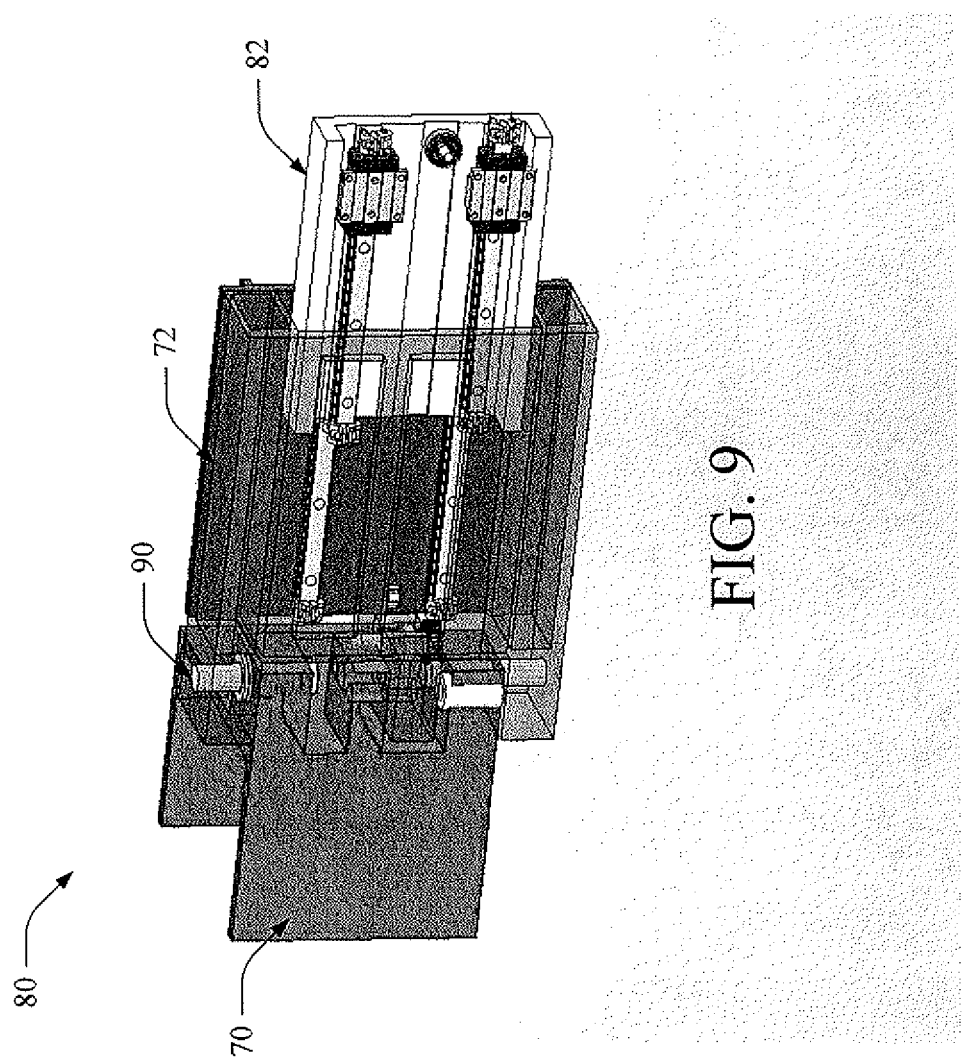
FIG. 9 illustrates the automatic locking mechanism in its fully extended position.

FIG. 9 illustrates the automatic locking mechanism 80 in its fully extended position. The extender arm 72 is pivoted about the hinge pin 90 outward from its stowed position against the mount 70, approximately 90°. The slider plate is extended outward from its stowed position in the extender arm. The motion of the slider plate is translated into rotational motion that actuates a locking pin screw, which extends a locking pin into a receiving bore to lock the extender arm and slider plate in the extended position.

Figure 10:
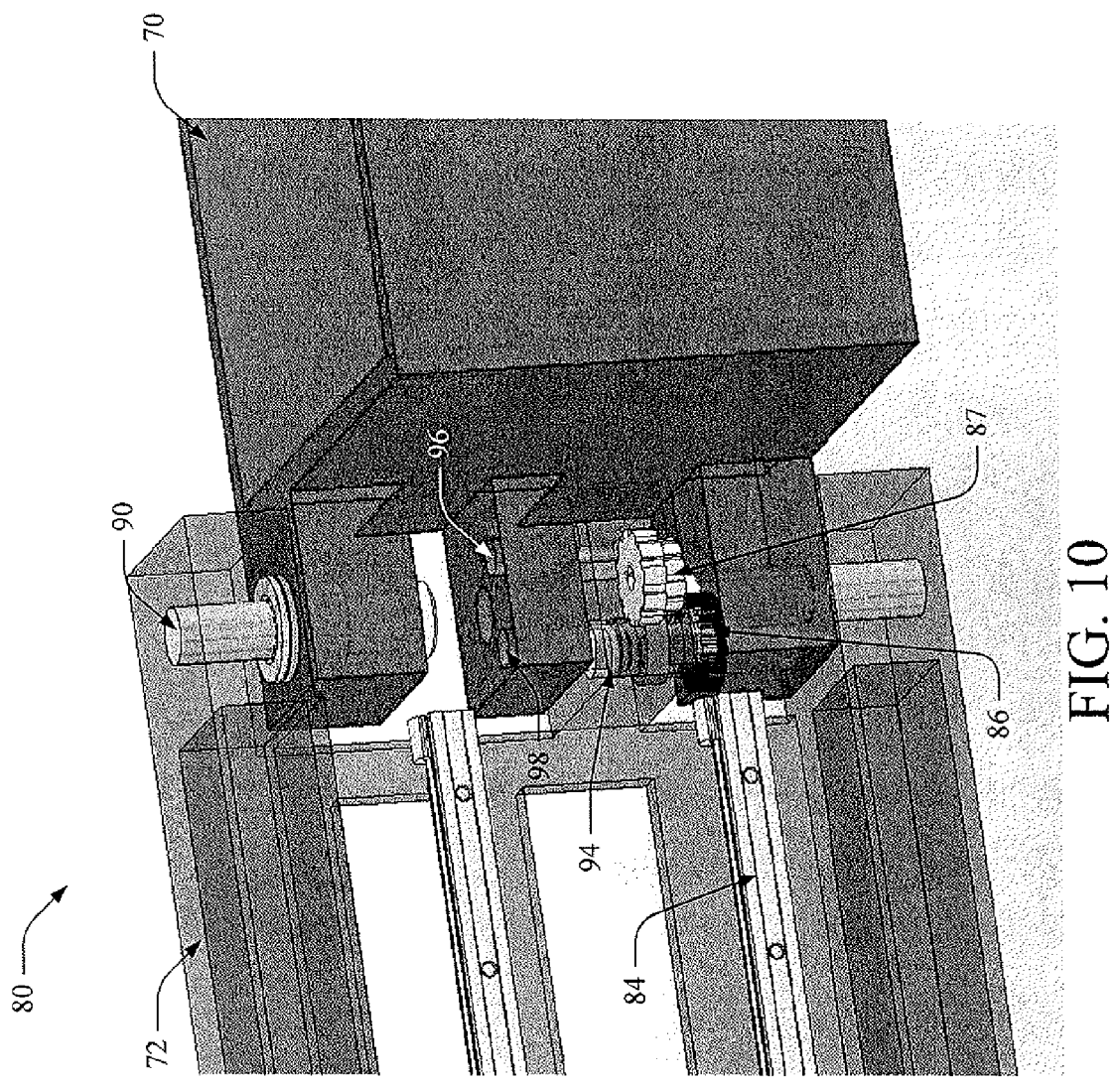
FIG. 10 illustrates the hinge portion of the automatic locking mechanism when the extender arm is in its extended position.

FIG. 10 illustrates the hinge portion of the automatic locking mechanism 80 when the extender arm 72 is in its extended position. The extender arm is rotated outward, about the hinge pin 90, from the mount 70. When the slider plate 82 is extended outward partially from the extender arm, a slider 84 actuates a first motion translator 86 to translate the linear motion of the slider into rotational motion that causes a locking pin screw 88 to be threaded out of a first receiving bore 96. The extender arm is then pivoted 90° outward from the mount, and the slider plate is fully extended from the extender arm. The complete extension of the slider plate causes the slider to engage a second motion translator 87, which causes the locking pin screw 88 to extend the locking pin 94 into a second receiving bore 98, which locks the extender arm into its extended position.

The following example illustrates the movement of the extender arm relative to the preceding figures. The automatic locking assembly for the flat panel detector is stowed in a position as shown in FIGS. 5 and 8. The locking pin 94 is engaged in the first receiving bore 96 in the corresponding hinge mating part. Thus, the extender arm 72 is locked in the folded position. As sliders 84 start to move out linearly to a first position, a motion translator 86 translates the linear motion to rotary motion, causing the locking pin screw 88 to be threaded out of the first receiving bore 96. At this point only portion of the travel of the slider plate is consumed, and the hinge is unlocked. The arm is then rotated approximately 90°, and the slider plate of the extender arm is pulled further out to a completely extended, or operational, position causing a second motion translator 87 to engage and rotate the screw 88 in an opposite direction to insert the locking pin into the second receiving bore 98. Thus, the hinge is locked again in the extended position as shown in FIGS. 6 and 7.

Accordingly, locking is achieved by translating the linear motion to rotary motion through a mechanism such as rack and pinion assembly as shown in FIG. 6. As the slider 84 moves in and out, the fine pitch screw system is turned and the locking pin 94 is inserted into one of the precision bores provided in the mating hinge, thereby eliminating a need to manually lock the flat panel monitor in a given position. Additionally, the mechanism provides a safeguard against an operator failing to lock the detector in position, because the mechanism automatically locks the detector in position.

In another embodiment, a power drive component (not shown) is included to perform automatic two-stage movement of the slider plate and rotation of the extender arm. The power drive can be controlled from a user interface (e.g., a computer or workstation) to move the detector between stowed and operational positions.

In another embodiment, a method of operating the system includes rotating the nuclear detector heads 18, the X-ray source 20, and the X-ray detector 22 around the patient pallet 14 such that the X-ray source and the nuclear detectors have overlapping or coincident fields of view. According to the method, the detector is locked in the operational position when CT acquisition is occurring, and locked in the stowed position when CT acquisition is not occurring (e.g., during nuclear image data acquisition or when the system is not in use. During CT imaging, truncated X-ray data of portions of the VOI 42 of a patient are collected such that views of the VOI are collected form 180° opposite orientations as the gantry 16 rotates. For instance, as the gantry rotates through a 180° point opposite its starting point, the X-ray source and detector begin generating opposing views of the VOI. In this manner, a complete data set is ensured, and redundant data can later be removed, before image reconstruction. Additionally, the X-ray detector is locket in place (e.g., in its operational position opposite the X-ray source) during CT acquisition. Once CT acquisition is complete, the X-ray source is folded out of the way, and the X-ray detector is folded and locked in a stowed position so that nuclear imaging data acquisition can begin. For instance, the detector is mounted to the slider plate 82, which is extended out of the extender arm 72 during CT operation. The slider plate can be retracted from the fully extended position to a partially extended position, and linear motion during the retracting of the plate can be translated into rotational motion by the motion translator 87. The rotational motion causes the locking pin screw 88 to turn, which pulls the locking pin out of the receiving bore 98 to unlock the detector from the operational position. Once the pin is out of the receiving bore 98, the extender arm is folded back against the mount 70. At this point, the slider plate is fully retracted into the extender arm, and the motion translator 86 translates the linear motion of the slider 84 into rotational motion that is applied to the locking pin screw, causing the locking pin to be inserted into the receiving bore 96 to lock the detector in the stowed position. The above actions can be performed in reverse to unlock the detector from the stowed position and lock it in the operational position whenever CT acquisition is to be performed.

Figure 11:
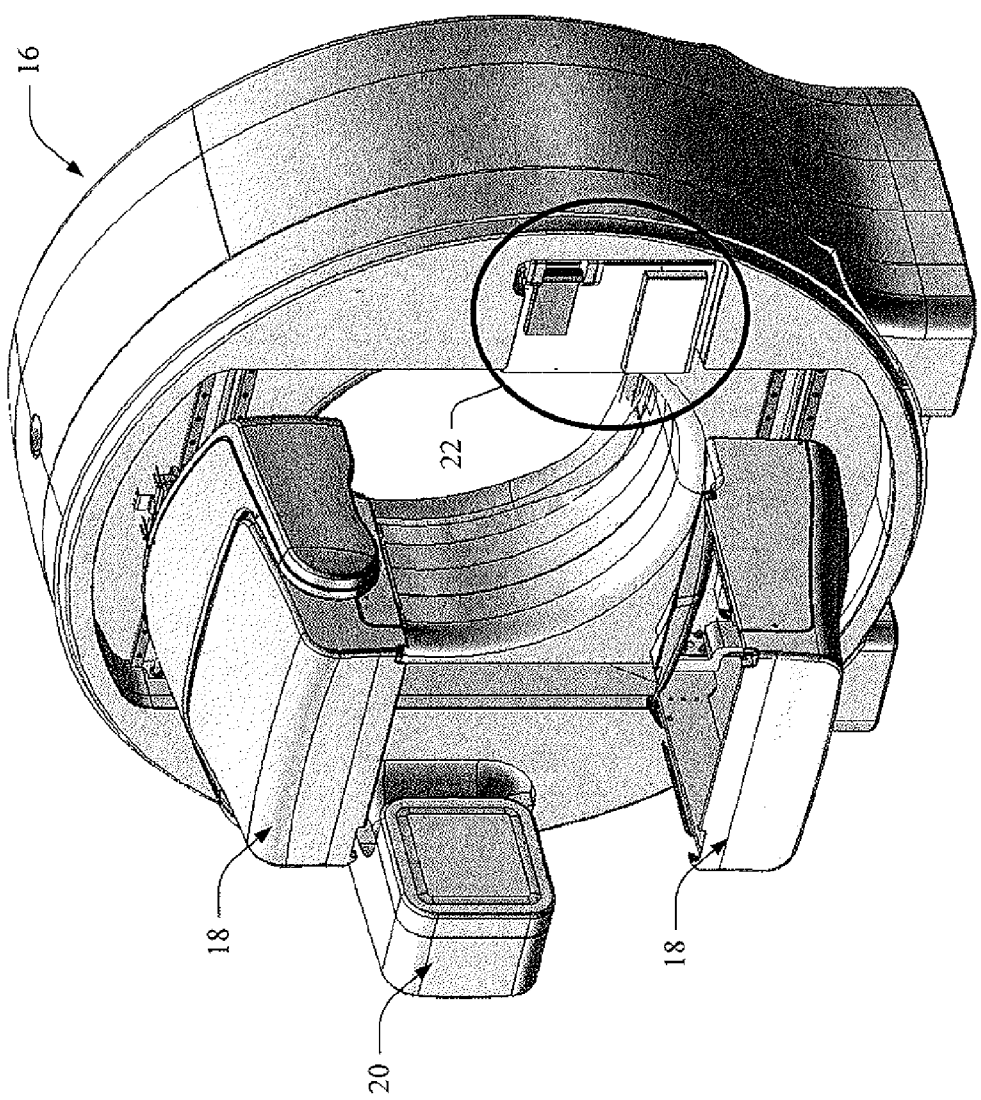
FIG. 11 is an illustration of the gantry with the nuclear detectors and the radiation source, which is shown opposite the flat panel X-ray detector.

FIG. 11 is an illustration of the gantry 16 with the nuclear detectors 18 and the radiation source 20, which is shown opposite the flat panel X-ray detector 22. The flat panel detector 22 is shown in its stored position, in the wall of the rotating gantry portion 26. By storing the flat panel detector in this manner, the flat panel detector 22 is out of the path of the nuclear detectors 18. Moreover, the flat panel detector is protected during, for example, collimator exchange, bed imaging, QC tuning of the nuclear detectors, as well as during shipping.

Figure 12:
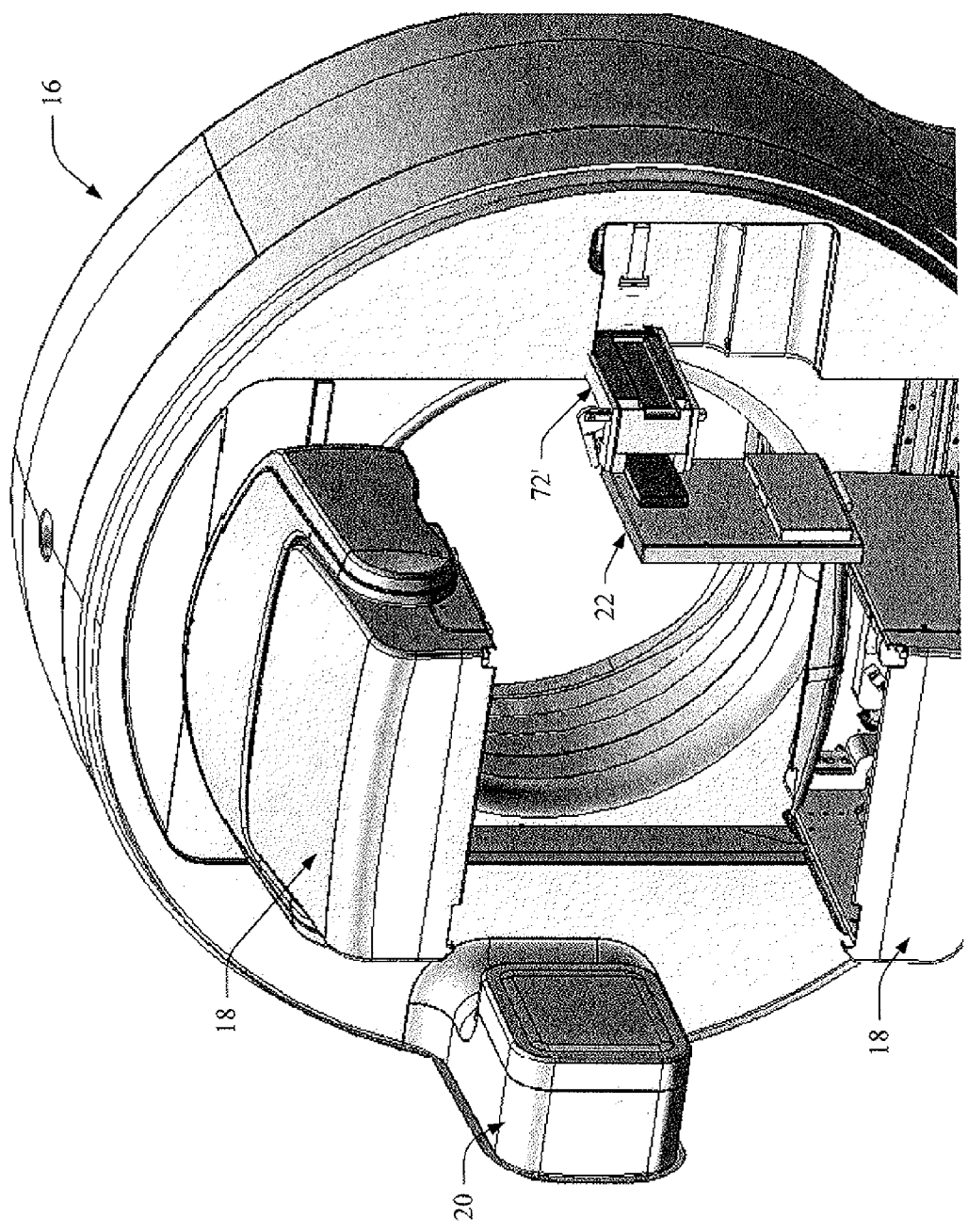
FIG. 12 is an illustration of the gantry, showing the nuclear detectors and the radiation source with the flat panel detector deployed.

FIG. 12 is an illustration of the gantry 16, showing the nuclear detectors 18 and the radiation source 20 with the flat panel detector 22 deployed. An extender arm 72' is folded outward from its stowed position in the surface of the gantry, and the flat panel detector is further folded outward from the extender arm so that a radiation-receiving surface thereof is facing the radiation source 20.

Figure 13A:
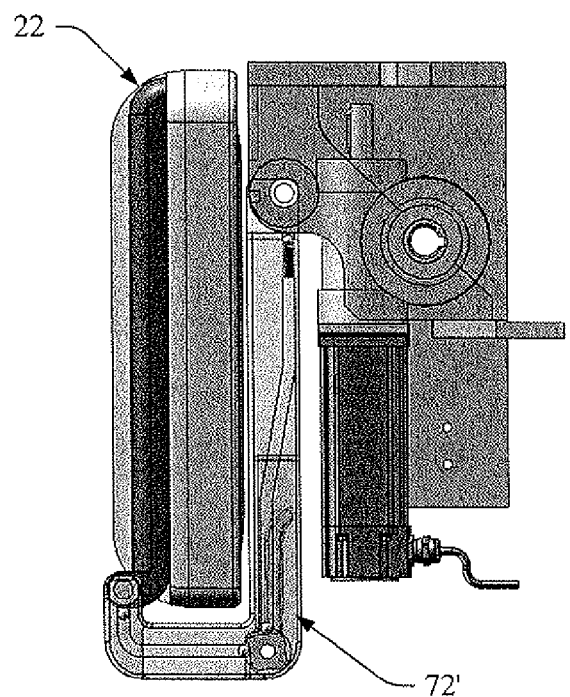
FIG. 13A illustrates the flat panel detector stored in a folded position against the extender arm, which is also in a folded stowed position.

FIGS. 13A-D illustrate top-down views of the flat panel detector 22 and extender arm 72' in various stages of deployment. In FIG. 13A, the flat panel detector 22 is stored in a folded position against the extender arm 72', which is also in a folded stowed position.

Figure 13B:
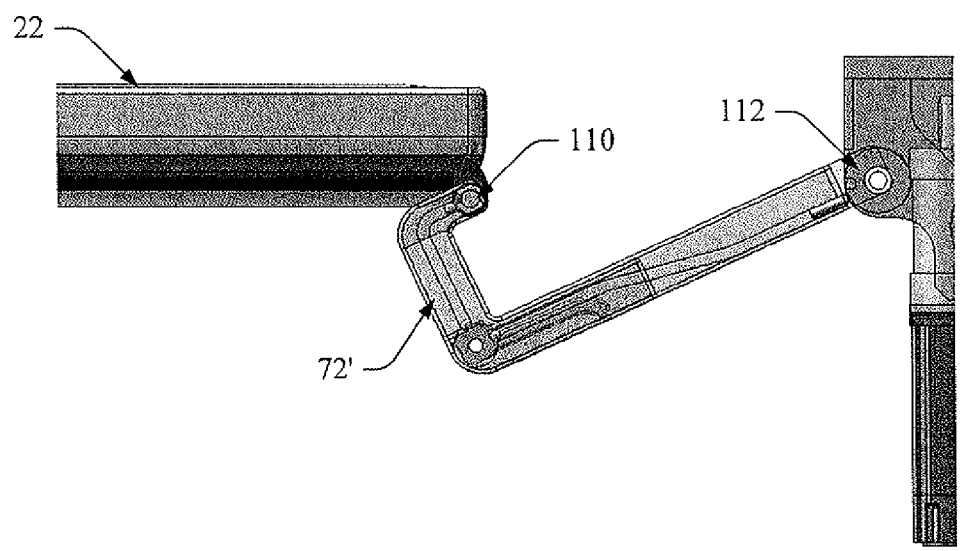
FIG. 13B illustrates the flat panel detector folded or rotated outward from the extender arm about a first pivot point or hinge.

In FIG. 13B, the flat panel detector 22 has been folded or rotated outward from the extender arm 72' about a first pivot or hinge 110. The extender arm 72' has been rotated or folded outward from its stowed position about a second pivot or hinge 112.

Figure 13C:
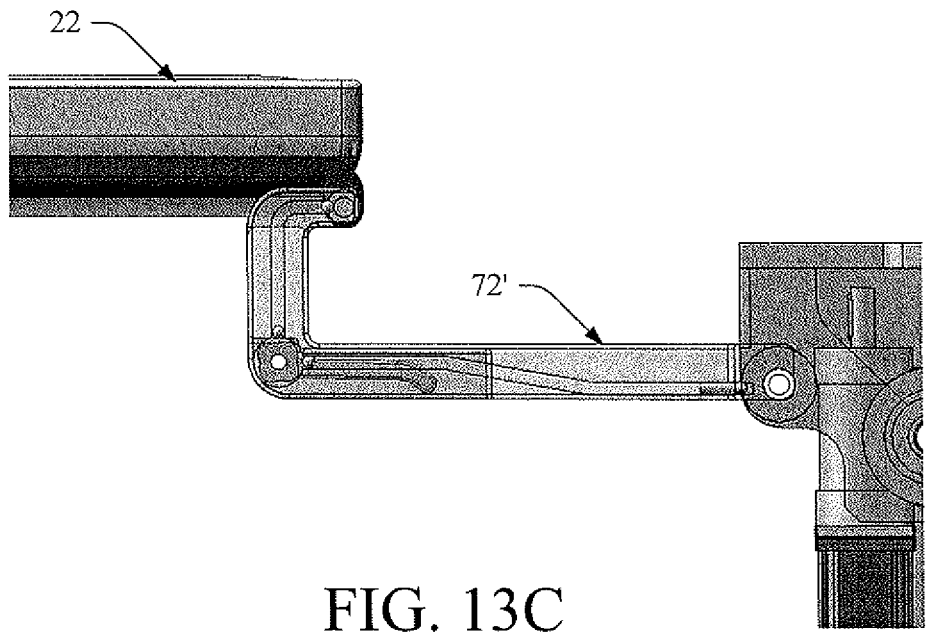
FIG. 13C illustrates the flat panel detector and the extender arm in fully extended positions, having been rotated outward from the stowed position to an operational position.

In FIG. 13C, the flat panel detector 22 and the extender arm 72' are in fully extended positions, having been rotated outward from the stowed position to an operational position in which the radiation-receiving surface of the flat panel detector is oriented to receive radiation from a radiation source (e.g., positioned opposite an examination region of the gantry).

Figure 13D:
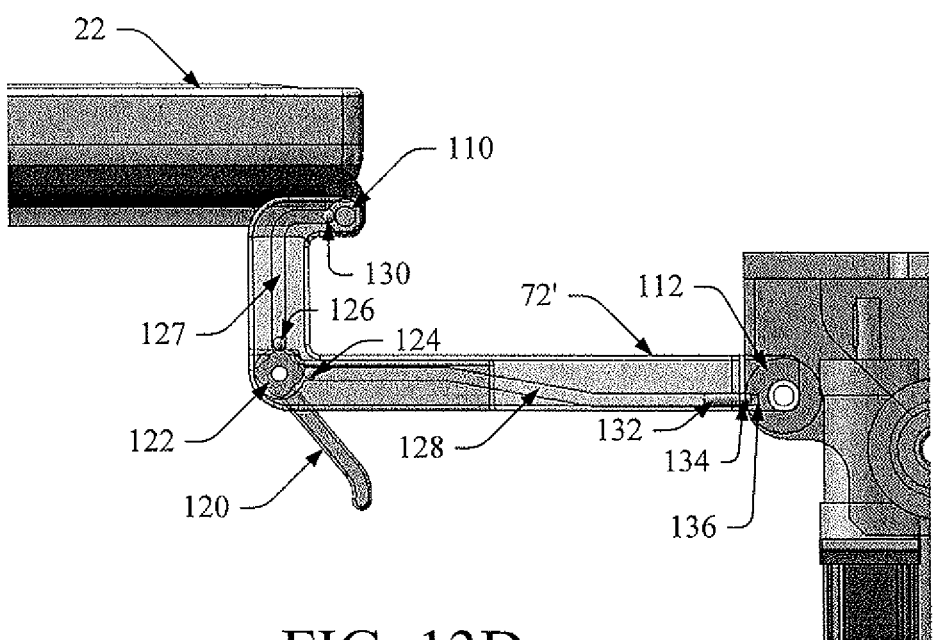
FIG. 13D illustrates the flat panel detector and the extender arm in a locked extended position.

In FIG. 13D, the flat panel detector 22 and the extender arm 72' are in a locked extended position. For instance, an operator pulls a handle 120 out from its stowed position in the extender arm 72' to lock the detector 22 in position. When the handle 120 is pulled outward, it activates a cam 122 in the extender arm, which in turn exerts a force on one or more balls or bearings 124, 126 positioned in one or more tracks 127, 128 internal to the extender arm 72'. In one embodiment, the tracks include a force transferring means (e.g., springs, rods, or the like) that transfer force between the balls upon activation of the cam. For instance, upon the cam exerting pressure on the ball 126, force is transferred via the track 127 to ball 130, which is in turn exerts a stopping force on pivot point 110, preventing the flat panel detector 22 from moving from its locked position. Similarly and concurrently, activation of the cam exerts pressure on ball 24, which transfers a force to a ball plunger 132 via the track 128. The ball plunger thus pushes a ball or bearing 134 into a ball-receiving groove 136 in the pivot point 112 to prevent the extender arm 72' from moving during operation. In this manner, the extender arm and flat panel detector are accurately, repeatably, and securely locked in an extended operational position by the dual-pivot point locking arrangement.

Figure 14:
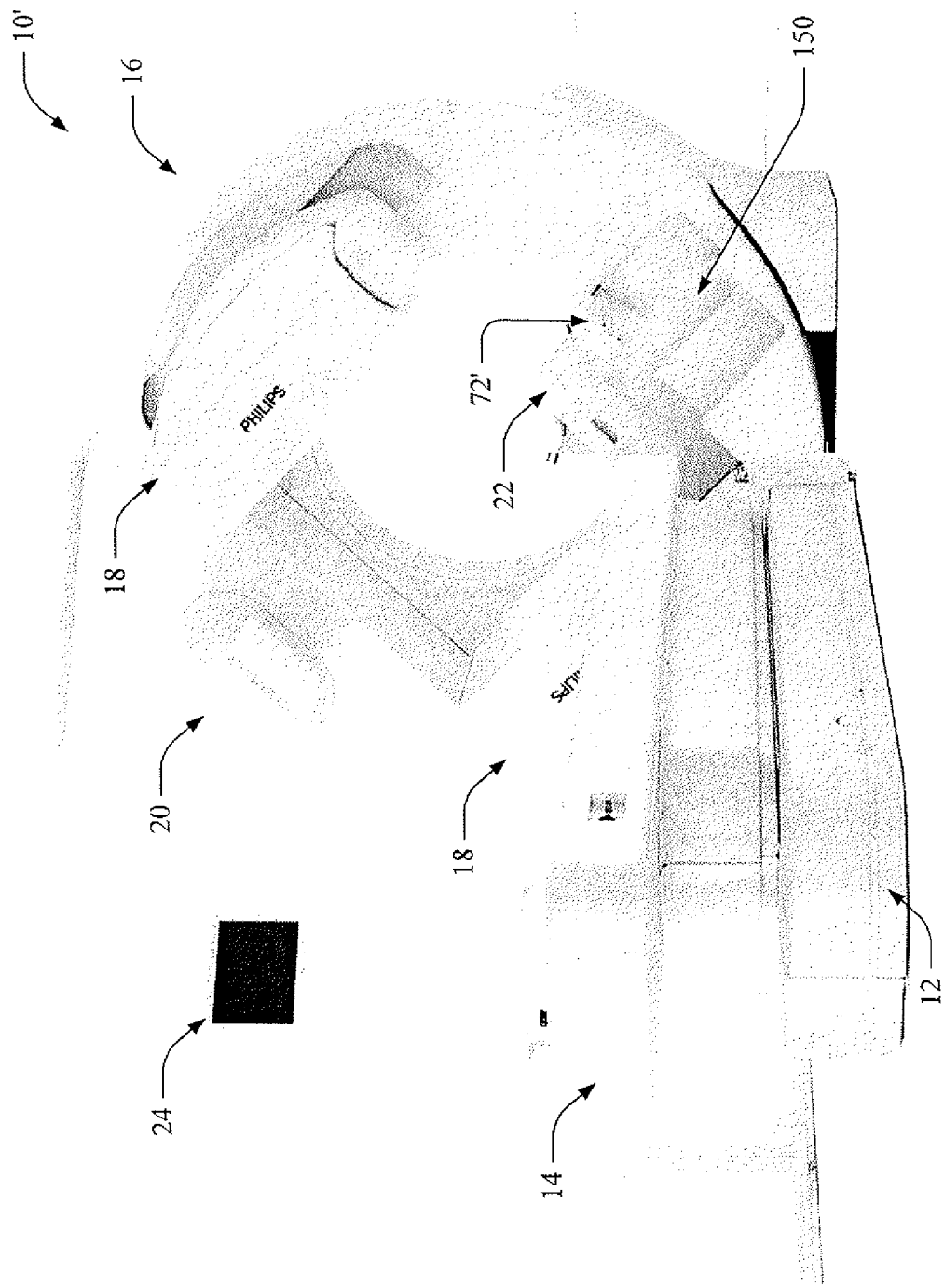
FIG. 14 illustrates an embodiment of the system with the lockable extender arm and flat paned detector assembly in an extended or operational position.

FIG. 14 illustrates an embodiment of the system 10' with the lockable extender arm and flat paned detector assembly in an extended or operational position. The system 10' includes the subject support 12 with a patient pallet 14 for translating a patient into and out of the examination region of the gantry 16. The pair of nuclear detector heads 18, the radiation source 20, and the flat panel detector 22 are mounted on the gantry 16. A monitor 24 is provided for viewing images of the subject generated by the system 10'. When not in use, the flat panel detector 22 is stowed into a receiving cavity 150, out of the way of the nuclear detectors 18. It will be appreciated that the components of the system 10' may be similar or identical to the components of the system 10 described with regard to FIGS. 1-5, and may further employ the extender arm 72' of FIGS. 12-13D.

The innovation has been described with reference to several embodiments. Modifications and alterations may occur to others upon reading and understanding the preceding detailed description. It is intended that the innovation be construed as including all such modifications and alterations insofar as they come within the scope of the appended claims or the equivalents thereof.

The invention claimed is:

1. A hybrid patient imaging system, including:
   at least two nuclear detector heads mounted on a rotatable gantry;
   an X-ray source mounted on the gantry;
   an X-ray detector mounted on the gantry opposite the X-ray source and offset relative to the X-ray source; and
   an automatic-locking extender arm, hingeably coupled to a mount on the gantry and to the X-ray detector head;
   wherein a field of view (FOV) of the X-ray source and a FOV of the nuclear detector heads overlap each other.

2. The system according to claim 1, wherein the X-ray source directs a cone-shaped X-ray beam to the offset X-ray detector.

3. The system according to claim 2, wherein a volume of interest (VOI) is positioned partially within the FOV of the X-ray source to generate truncated views, and the gantry is rotated approximately 360° around the VOI during CT data acquisition, the FOV is truncated such that truncated 180° opposing views taken together generate a complete projection data set for the VOI.

4. The system according to claim 3, wherein the X-ray source is movable longitudinally along the VOI, parallel to a longitudinal axis through the center of the gantry, as the gantry is rotated during CT data acquisition.

5. The system according to claim 4, wherein the X-ray detector is mounted longitudinally, parallel to the longitudinal axis of the rotating gantry.

6. The system according to claim 1, wherein at least one of the X-ray source and the X-ray detector are pivotably mounted to the rotating gantry to be rotated behind a front of the rotating gantry when not in use.

7. The system according to claim 1, wherein the X-ray detector is a flat panel detector.

8. The system according to claim 1, wherein the nuclear detector heads are at least one of single photon emission computed tomography (SPECT) detector heads or positron emission tomography (PET) detector heads.

9. The system according to claim 1, wherein the extender arm includes a hinge pin that extends through hinge segments coupled to the mount and the extender arm, respectively, and wherein the extender arm is folded flush against the mount when stowed, and folded outward approximately 90° to an operation position when in use.

10. The system according to claim 1, wherein the extender arm includes a slider plate with at least one slider mounted thereon, and wherein the at least one slider actuates a first motion translator when the slider plate is partially extended out of the extender arm.

11. The system according to claim 10, wherein the first motion translator causes a locking pin screw to disengage a locking pin from a first receiving bore in a hinge mating part of a hinge assembly.

12. The system according to claim 10, wherein the extender arm is rotated into the operational position and wherein the at least one slider actuates a second motion translator as the slider plate is completely extended out of the extender arm.

13. The system according to claim 12, wherein the second motion translator causes the locking pin screw to advance the locking pin into a second receiving bore to lock the extender arm in the operational position.

14. The system according to claim 1, further including:
   wherein the extender arm is coupled to the X-ray detector at a first pivot point and mounted to the gantry at a second pivot point; and
   a handle on the extender arm that, when pulled, activates a cam in the extender arm;
   wherein the X-ray detector rotates about the first pivot point from a stowed position against the extender arm, and the extender arm rotates about the second pivot point from a stowed position between the X-ray detector and surface of the gantry, until the X-ray detector is in an operational position opposite the X-ray source;
   wherein activation of the cam causes the cam to exert force on first and second bearings, the force being translated from the first and second bearings along tracks to third and fourth bearings and causing the third and fourth bearings to exert a locking force on the first and second pivot points, respectively, to lock the X-ray detector in the operational position.

15. A hybrid subject imaging system, including:
   an automatic-locking extender arm, hingeably coupled by a hinge pin to a mount on a rotatable gantry and including an extendible slider plate that is coupled to a flat-panel X-ray detector;
   a cone-beam X-ray source coupled to the gantry opposite the X-ray detector, the X-ray source being movable in a longitudinal direction along a volume of interest (VOI), parallel to a longitudinal axis through the gantry;
   two nuclear detectors coupled to the gantry and having a field of view (FOV) that overlaps with a FOV of the X-ray source;
   wherein the extender arm rotates about the hinge pin approximately 90° between a stowed position flush against the mount and an operational position in which an X-ray receiving surface of the X-ray detector is slightly offset from, and faces, the X-ray source.

16. The system according to claim 15, wherein the extender arm includes a slider plate with at least one slider mounted thereon, which actuates a first motion translator when the slider plate is partially extended out of the extender arm.

17. The system according to claim 16, wherein the first motion translator causes a locking pin screw to retract a locking pin from a first receiving bore.

18. The system according to claim 17, wherein the extender arm is rotated into the operational position once the locking pin is retracted form the first receiving bore and the at least one slider actuates a second motion translator as the slider plate is completely extended out of the extender arm.

19. The system according to claim 15, wherein the second motion translator causes the locking pin screw to advance the locking pin into a second receiving bore to lock the extender arm in the operational position.

20. The system according to claim 19, wherein a volume of interest (VOI) is positioned partially within the FOV of the X-ray source to generate truncated views, and the gantry is rotated approximately 360° around the VOI during CT data acquisition, the FOV is truncated such that truncated 180° opposing views taken together generate a complete projection data set for the VOI.

21. A method of hybrid imaging, comprising:
rotating at least two nuclear detector heads, an X-ray source, and an X-ray detector around a patient pallet such that a field of view of the X-ray source and detector is coincident with a field of view of the nuclear detector heads; and
during CT imaging, collecting truncated portions of a volume of interest (VOI) of a patient in such a manner that views from opposite halves of the VOI are collected in 180° opposite rotational orientations of a rotating gantry;
wherein the X-ray detector is coupled to the gantry by an automatic-locking extender arm.

22. The method according to claim 21, further including:
prior to acquiring data with the nuclear detector heads, folding the X-ray source and detector out of the way.

23. The method according to claim 22, further including locking the detector in a stowed position by:
retracting a slider plate from a second position wherein a second motion translator translates linear motion from a slider coupled to the slider plate into rotational motion that is applied to a locking pin screw to translate a locking pin out of a second receiving bore and unlock the detector from an operational position;
rotating the extender arm approximately 90° from the operational position to the stowed position; and
retracting the slider plate inward to a first position in an extender arm that is coupled to a mount on a gantry, wherein a first motion translator translates linear motion from the slider coupled to the slider plate into rotational motion that is applied to the locking pin screw to insert the locking pin into a first receiving bore and lock the detector in the stowed position.

24. A hybrid subject imaging system, including:
a locking extender arm, rotatably coupled by a first pivot point to a flat-panel X-ray detector and rotatably coupled by a second pivot point to a rotatable gantry;
a cone-beam X-ray source coupled to the gantry opposite the X-ray detector, the X-ray source being movable in a longitudinal direction along a volume of interest (VOI), parallel to a longitudinal axis through the gantry;
one or more nuclear detectors coupled to the gantry and having a field of view (FOV) that overlaps with a FOV of the X-ray source;
wherein the extender arm rotates about the second pivot point approximately 90° between a stowed position flush against the gantry, and the flat-panel X-ray detector rotates about the second pivot point approximately 180°, to an operational position in which an X-ray receiving surface of the X-ray detector is slightly offset from, and faces, the X-ray source.

25. The system according to claim 24, further including:
a handle on the extender arm that, when pulled, activates a cam in the extender arm;
wherein activation of the cam causes the cam to exert force on first and second bearings, the force being translated from the first and second bearings along force transferring means to third and fourth bearings and causing the third and fourth bearings to exert a locking force on the first and second pivot points, respectively, to lock the X-ray detector in the operational position.

26. A hybrid patient imaging system, including:
at least two nuclear detector heads mounted on a rotatable gantry;
an X-ray source mounted on the gantry; and
an X-ray detector mounted on the gantry opposite the X-ray source and offset relative to the X-ray source;
wherein a field of view (FOV) of the X-ray source and a FOV of the nuclear detector heads overlap each other;
wherein the X-ray source directs a cone-shaped X-ray beam to the offset X-ray detector; and
wherein a volume of interest (VOI) is positioned partially within the FOV of the X-ray source to generate truncated views, and the gantry is rotated approximately 360° around the VOI during CT data acquisition, the FOV is truncated such that truncated 180° opposing views taken together generate a complete projection data set for the VOI.

27. The system according to claim 26, wherein the X-ray source is movable longitudinally along the VOI, parallel to a longitudinal axis through the center of the gantry, as the gantry is rotated during CT data acquisition.

28. The system according to claim 27, wherein the X-ray detector is mounted longitudinally, parallel to the longitudinal axis of the rotating gantry.

29. A method of hybrid imaging, comprising:
rotating at least two nuclear detector heads, an X-ray source, and an X-ray detector around a patient pallet such that a field of view of the X-ray source and detector is coincident with a field of view of the nuclear detector heads; and
during CT imaging, collecting truncated portions of a volume of interest (VOI) of a patient in such a manner that views from opposite halves of the VOI are collected in 180° opposite rotational orientations of a rotating gantry; and
prior to acquiring data with the nuclear detector heads, folding the X-ray source and detector out of the way.

30. The method according to claim 29, further including locking the detector in a stowed position by:
retracting a slider plate from a second position wherein a second motion translator translates linear motion from a slider coupled to the slider plate into rotational motion that is applied to a locking pin screw to translate a locking pin out of a second receiving bore and unlock the detector from an operational position;
rotating an extender arm approximately 90° from the operational position to the stowed position; and
retracting the slider plate inward to a first position in an extender arm that is coupled to a mount on a gantry, wherein a first motion translator translates linear motion from the slider coupled to the slider plate into rotational motion that is applied to the locking pin screw to insert the locking pin into a first receiving bore and lock the detector in the stowed position.

* * * * *